(12) United States Patent
Aifer et al.

(10) Patent No.: US 8,685,273 B2
(45) Date of Patent: Apr. 1, 2014

(54) ETCHING AGENT FOR TYPE II INAS/GAINSB SUPERLATTICE EPITAXIAL MATERIALS

(71) Applicants: Edward H Aifer, Arlington, VA (US); Sergey I Maximenko, Alexandria, VA (US)

(72) Inventors: Edward H Aifer, Arlington, VA (US); Sergey I Maximenko, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/669,663

(22) Filed: Nov. 6, 2012

(65) Prior Publication Data

US 2013/0122715 A1 May 16, 2013

Related U.S. Application Data

(60) Provisional application No. 61/559,430, filed on Nov. 14, 2011.

(51) Int. Cl.
*C09K 13/08* (2006.01)

(52) U.S. Cl.
USPC ............................. 252/79.3; 216/96; 438/745

(58) Field of Classification Search
USPC ............. 216/83, 96; 438/745; 252/79.1, 79.2, 252/79.3
See application file for complete search history.

(56) References Cited

U.S. PATENT DOCUMENTS

| 4,100,014 A | 7/1978 | Kuhn-Kuhnenfeld et al. |
| 4,459,216 A | 7/1984 | Nakazato et al. |
| 2006/0086372 A1 | 4/2006 | Mellies et al. |

OTHER PUBLICATIONS

J. Doershel and U. Geissler; J. Cryst. Growth, 121, 781 (1992).
Costa et al. (E.M. Costa, B.A. Dedavid, and A. Muller; Mater. Sci. Eng. B, B44, 208 (1991).
G.T. Brown, B. Cockayne, W.R. Macewan and V.W. Steward; "A defect etchant for single crystal GaSb"; J. Mater. Sci. Lett. 1, 253 (1982).
A. Clawson; "Guide to references on III-V semiconductor chemical etching"; Mater. Sci. Eng. 31, 1 (2001).
I. Yonenaga; "Dynamic behavior of dislocations in InAs: in comparison with III-V compounds and other semiconductors"; J. Appl. Phys. 84, 4209 (1998).

*Primary Examiner* — Roberts Culbert
(74) *Attorney, Agent, or Firm* — US Naval Research Laboratory; Stephen T. Hunnius

(57) ABSTRACT

This disclosure involves a formula, mixing procedure, etching technique and application of an etchant for revealing defects in T2SL's grown lattice matched to (100) GaSb. The etching agent comprises a (2.5:4.5:16.5:280) solution by volume or (1%:2%:9%:88%) by weight, of $HF:H_2O_2:H_2SO_4:H_2O$. The etchant is made by mixing (49%) hydrofluoric aqueous solution with (30%) water-based peroxide, followed by sulfuric acid, and diluted with de-ionized H2O (DI-water).

14 Claims, 5 Drawing Sheets

ETCHING AGENT FOR TYPE II INAS/GAINSB SUPERLATTICE EPITAXIAL MATERIALS

CROSS-REFERENCE TO RELATED APPLICATIONS

This application is a non-provisional application of and claims priority to and benefits of U.S. Patent Application No. 61/559,430 filed Nov. 14, 2011, which is herein incorporated by reference in the entirety.

BACKGROUND OF THE INVENTION

1. Field of the Invention

The disclosure involves a formula, mixing procedure, etching technique and application of an etchant for revealing defects in a Type II superlattice matched to (100) GaSb.

2. Description of Related Art

One aspect of this disclosure involves a method for revealing crystallographic defects on the (100) face of Type II InAs/GaInSb based superlattice structures by preferential wet chemical etching.

Type II InAs/$Ga_{1-x}In_xSb$ superlattices (T2SLs) lattice matched to GaSb substrates (x typically ≤20%) are an important semiconductor heterostructure material systems for applications in mid-, long- and very long-wave infrared detectors. They have theoretical performance limits well beyond those of incumbent technologies based on InSb and HgCdTe.

T2SLs were first introduced in the 1970s by Sai-Halasz, Tsu and Esaki, and then a decade later, were proposed by Smith and Mailhiot to be used for infrared detection. Presently, state-of-the-art T2SL material is grown using molecular beam epitaxy (MBE) on (100) GaSb substrates.

The period structure of the basic binary form of T2SL consists of a pair of 1 to 5 nm-thick InAs and GaSb layers. Approximately one additional monolayer (ML) of InSb ($\alpha$=6.4794 Å) is also required in each period to balance the strain with respect to the GaSb substrate ($\alpha$=6.0959 Å) resulting from the shorter lattice constant of InAs ($\alpha$=6.0583 Å).

The ternary T2SL is an alternate form in which GaSb is replaced by Ga(1-x)In(x)Sb in the superlattice, and strain is balanced by adjusting the InSb-alloy fraction "x" in the ternary layer and dispensing with the half-ML of InSb at each interface. These and several other types of T2SLs may be readily doped n- or p-type, and have been used to construct an enormous variety of infrared sensor structures, with epitaxial thicknesses of up to ~15 μm's.

Despite more than 30 years of study, however, T2SL technology has not yet achieved its full theoretical promise, largely due to the presence of bulk and surface crystallographic defects generated during MBE growth and device fabrication that promote excess dark current.

Progress in understanding the nature of these defects and how to remediate them has been hindered by the difficulty in identifying specific defect structures in this material system.

One widely used technique that has been used successfully to identify defects with densities of up to ~$10^5$ $cm^{-2}$ on substrates and epitaxial material, is preferential chemical etching. Here, defect structures are identified by subjecting the material to a wet chemical etch that has the characteristic of being amplified in the presence of crystallographic defects, and then analyzing the density, location and physical structure of resulting etch pits.

Though a number of techniques exist to preferentially etch GaSb and InAs on different crystallographic planes, no such techniques have heretofore existed for superlattices composed of periodic combinations of thin layers of these materials. This is due to the fact that though InAs and GaInSb belong to the same −43 m point symmetry group, the difference in chemical composition yields a large contrast in preferential etch rates of these materials.

For etch pit defect delineation in (100) GaSb for example, a two-step etch process was used by J. Doershel, and U. Geissler where the surface was first chemically polished in a 2:18:40 (volume ratio) solution of $HF:HNO_3:CH_3COOH$, followed by etching in 2:1 solution of $HCl:H_2O_2$. Constant vigorous agitation was necessary to obtain reliable results.

Costa et al. used a (5:1) solution of $H_2SO_4:H_2O_2$ as well as (5:1) $CrO_3$ (5 M aqua. solution.):HF for etch pit delineation on GaSb (100). For preferential etching of InAs (111) orientation, Yonenaga employed a $2.4 \times 10^{-3}$ molar solution of $AgNO_3$ in (3:2:5) $HNO_3:HF:H_2O$.

We have found no previously published data, however, on preferential etching of InAs/GaInSb superlattices, indicating the lack of a common etching solution with similar preferential etch rates for both compound materials.

Thus we submit this disclosure of a single etchant which reveals and distinguishes crystallographic defects on (100) T2SLs through etch pit structures defined by preferential wet chemical etching.

BRIEF SUMMARY OF THE INVENTION

This disclosure involves a formula, mixing procedure, etching technique and application of an etchant for revealing defects in T2SL's grown lattice matched to (100) GaSb.

DETAILED DESCRIPTION OF THE INVENTION

Figure 1:
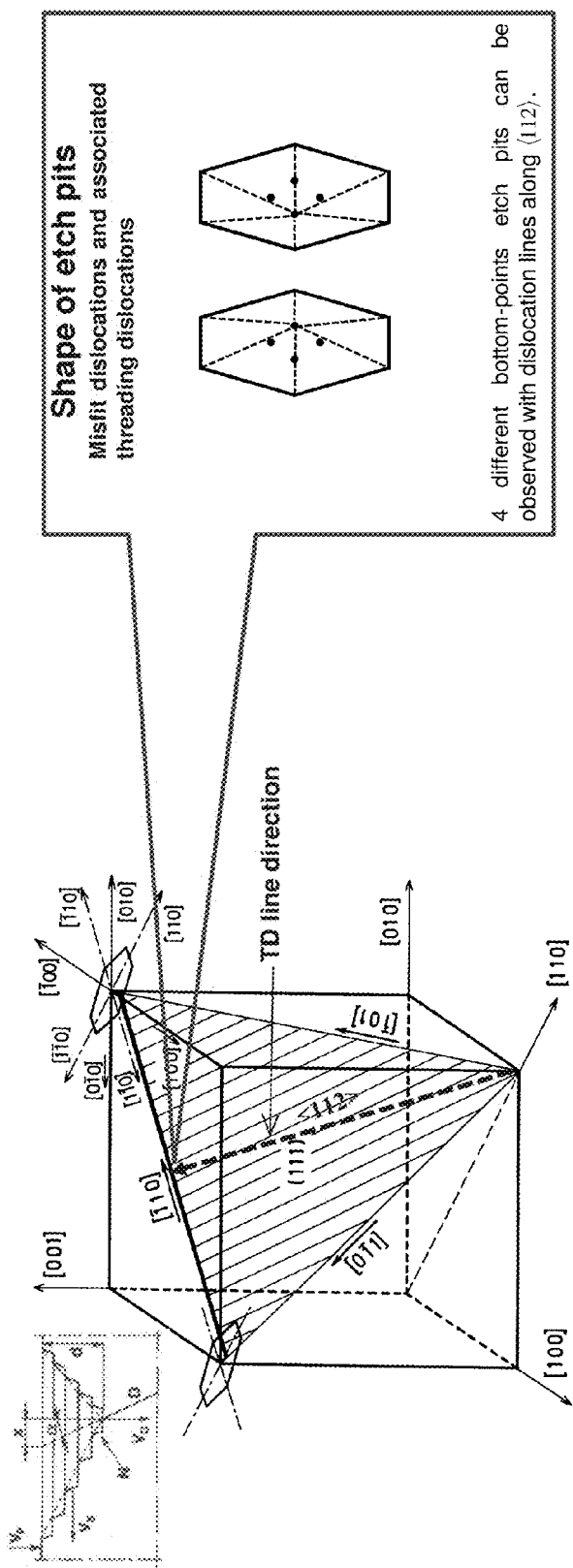
FIG. 1 illustrates GaSb, InAs (F-43 m space group), Zinc-Blende Lattice.
Figure 2:
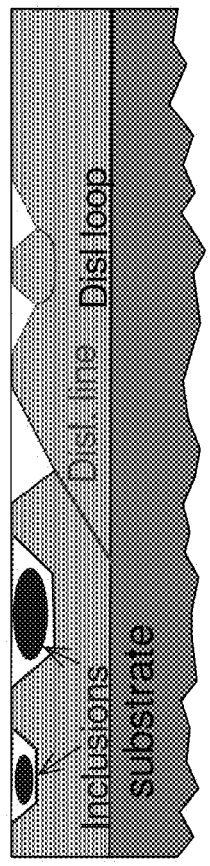
FIG. 2 illustrates etch pits from inclusion and etch pits from dislocations in the film.
Figure 3:
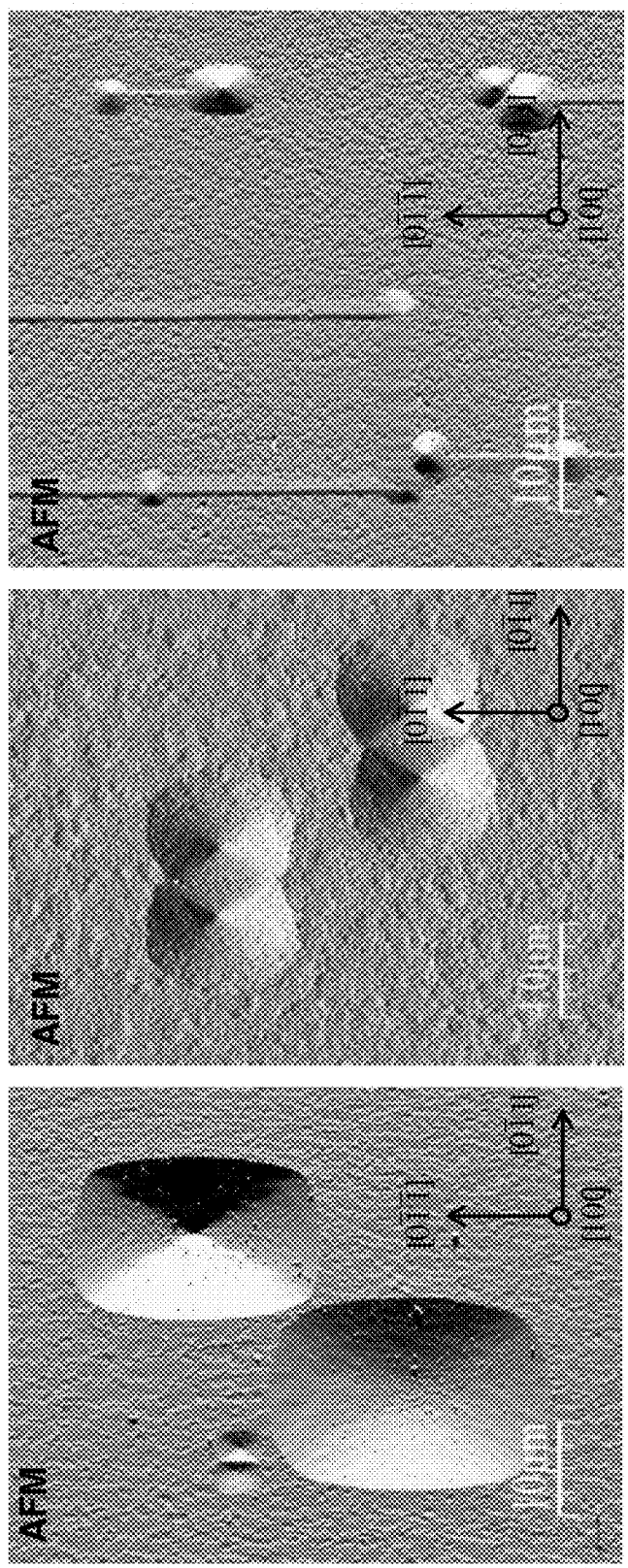
FIG. 3 illustrates typical etch pits in type II TSL.
Figure 4:
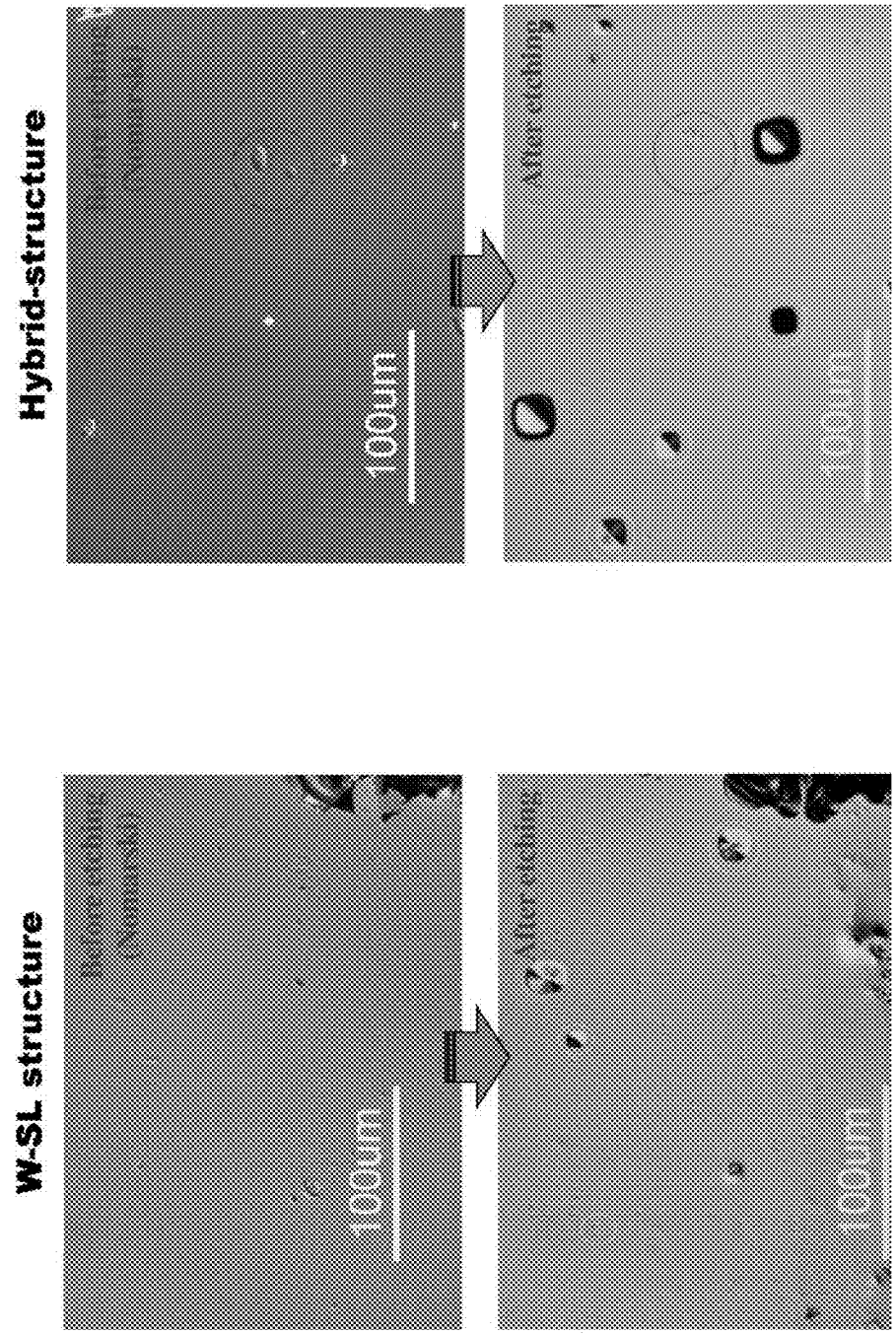
FIG. 4 illustrates chemical etching results of raw wafers. Rectangular etch pits with well-defined crystallographic facets form in locations containing dislocations in the crystal structure.
Figure 5:
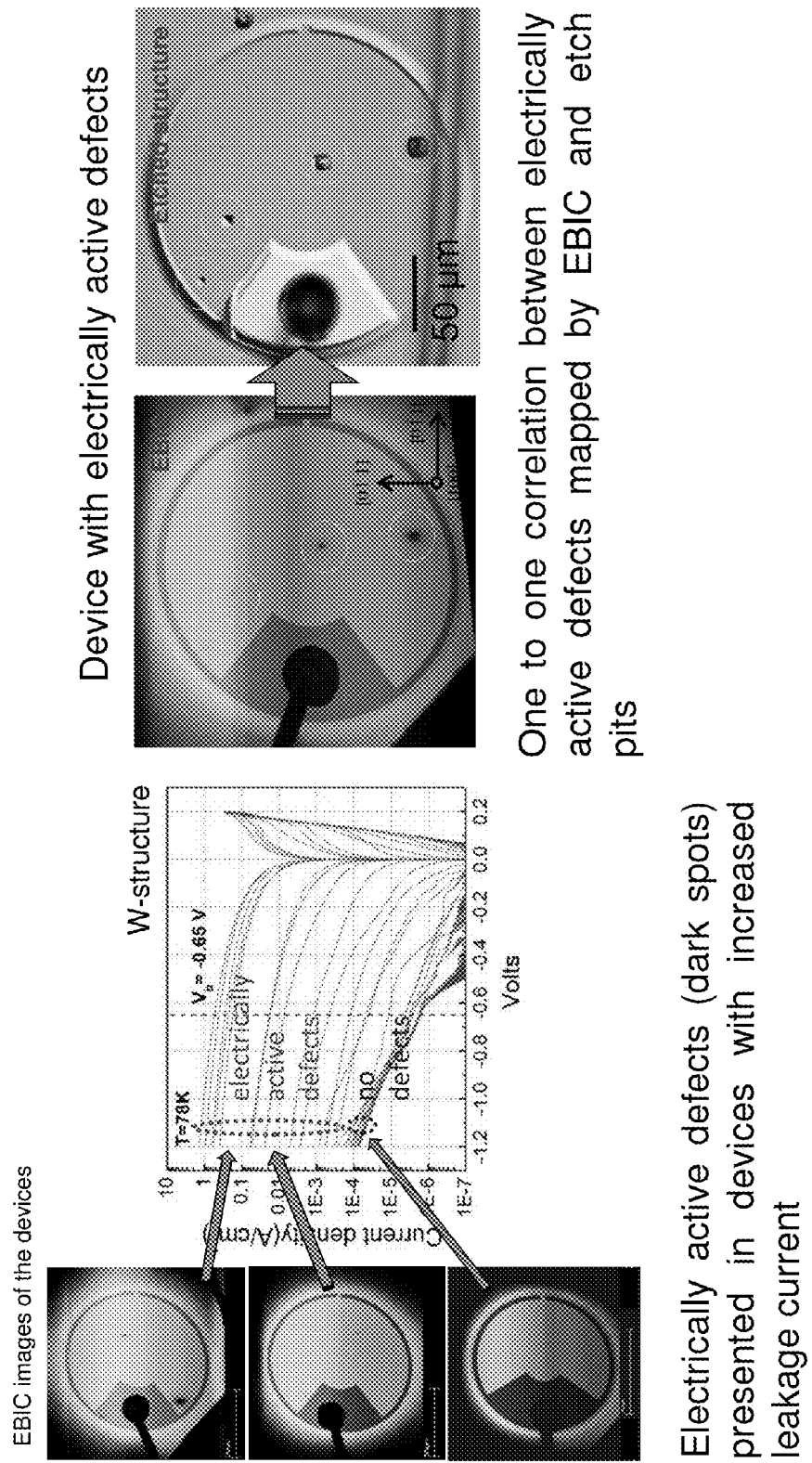
FIG. 5 illustrates correlation between electrically active defects, leakage current and etch pits. Shown are electrically active defects (dark spots) presented in devices with increased leakage current. Also shown is one to one correlation between electrically active defects mapped by EBIC and etch pits.

This disclosure involves a formula, mixing procedure, etching technique and application of an etchant for revealing defects in T2SL's grown lattice matched to (100) GaSb.

The etching agent comprises a (2.5:4.5:16.5:280) solution by volume or (1%:2%:9%:88%) by weight, of $HF:H_2O_2:H_2SO_4:H_2O$.

The etchant is made by mixing (49%) hydrofluoric aqueous solution with (30%) water-based peroxide, followed by sulfuric acid, and diluted with de-ionized H2O (DI-water).

Etching can be carried out at room temperature (around 20° C.), without stirring.

Typical etching times for the (100) face of a T2SL are in the range of 60-90 seconds.

After etching, the samples are rinsed thoroughly in DI-water and then dried using $N_2$ gas.

Under these conditions, using a freshly prepared solution, rectangular etch pits with well-defined crystallographic facets form in locations containing dislocations in the crystal structure. The resulting etch pits are oriented with the longest axis aligned along the [0 $\bar{1}$ $\bar{1}$] crystallographic direction.

The morphology of the etch pits and surface may be varied by adjusting the ratios of the etching solution from the mixture given above. For example, increasing the HF or $H_2O_2$ content leads to a more isotropic etch, with rounded etch pits. Increasing $H_2SO_4$ or decreasing HF content introduces more anisotropic etching of the surface. In addition, increasing $H_2SO_4$ or decreasing HF introduces nonuniform etching of the surface, making reliable identification of defects difficult.

Etching time is controlled by dilution with water, and for a typical long-wave infrared T2SL etched in the above solution with 88% DI-water by weight, etch pits ranging from 4-20 μm in diameter are formed after 60-90 seconds. Etch pits of this size are readily observed using optical differential interference contrast (Nomarski) microscopy.

The application of this novel etchant on T2SLs enables the detection and identification of various imperfections in the crystalline structure of the material, as etch pit formation is promoted and governed by the structure of the underlying defect.

For example, threading dislocations are indicated by large, deep rectangular pits, having bottom point symmetries reflecting dislocation direction. Misfit dislocations (half-loop arrays) are marked by twin shallow rectangular etch pits indicating the termination points of the half loops at the surface. More rounded, flat bottomed pits correspond to agglomerations of impurities.

In addition, the etch produces linear striations aligned along [01 $\bar{1}$] and [$\bar{1}$ 10] directions in the presence of stacking faults in (01 $\bar{1}$) and ($\bar{1}$ 10) glide planes.

The correlation between etch-pit structure, the structure of the underlying crystallographic defect, and the activity level of the defect with respect to dark current, were studied using electron beam induced current (EBIC) mapping of defects and cross-sectional transmission electron microscopy (TEM) to reveal the defect structure.

TEM and EBIC confirmed strong correspondence between etch pit and crystallographic defect structure. We found no other published data showing successful preferential etching of InAs/GaInSb superlattices, though a mixture of HF:$H_2O_2$:$H_2SO_4$:$H_2O$ has been reported for preferential etching of dislocations on $GaAs_xP_{1-x}$ semiconductors where x is in the range of 0 to 1 and consisted of HF:$H_2O_2$:$H_2SO_4$:$H_2O$ (6-18%:6-20%:20-55%:30-55%) by weight.

We tested several etchants suggested for preferential etching of GaSb and InAs, including a modified two-step etch process of Doershel et al. consisting of an initial polish in HF:$HNO_3$:$CH_3COOH$ (2:18:40) followed by etch-pit delineation in HCl: $H_2O_2$ (2:1).

Upon testing, it was found that this procedure generally produced a highly non-uniform surface against which etched features were difficult to discern.

The best performance was achieved by diluting the polishing etch as HF:$HNO_3$:$CH_3COOH$:$H_2O$ (2:18:40:30) by volume, and eliminating the second etch step HCl: $H_2O_2$ (2:1) entirely.

While dilution lowered the etch rate improving control, etch pit definition was marginal however as the increased water content also heavily degraded the shape of the etch pits as the etch became more isotropic. As a result, dilution was limited to a level with etching times of only 10-20 seconds, making control of the etching process difficult. Constant vigorous agitation of the etch bath was also necessary to remove gaseous products nucleated on the sample surface.

As such, our discovery overcame such problems and produced the best results. Our formula, mixing procedure, etching technique and application of an etchant for revealing defects in T2SL's grown lattice matched to (100) GaSb are herein disclosed. The etching agent can comprise a (2.5:4.5:16.5:280) solution by volume or (1%:2%:9%:88%) by weight, of HF:$H_2O_2$:$H_2SO_4$:$H_2O$ and, as discussed, variations are possible.

The above description is that of a preferred embodiment of the invention. Various modifications and variations are possible in light of the above teachings. It is therefore to be understood that, within the scope of the appended claims, the invention may be practiced otherwise than as specifically described. Any reference to claim elements in the singular, e.g., using the articles "a," "an," "the," or "said" is not construed as limiting the element to the singular.

What we claim is:

1. An etchant comprising:
   a (2.5:4.5:16.5:280) solution by volume of HF:$H_2O_2$:$H_2SO_4$:$H_2O$.

2. A solution for etching type II InAs/GaInSb superlattice epitaxial materials comprising:
   a (1%:2%:9%:88%) solution by weight HF:$H_2O_2$:$H_2SO_4$:$H_2O$.

3. A method of making a solution for etching type II InAs/GaInSb superlattice epitaxial materials comprising:
   mixing a hydrofluoric aqueous solution with a water-based peroxide to form a first solution;
   mixing the first solution with sulfuric acid to form a second solution;
   diluting the second solution with de-ionized water; and
   forming a (2.5:4.5:16.5:280) solution by volume of HF:$H_2O_2$:$H_2SO_4$:$H_2O$.

4. The method of making of claim 3 wherein the hydrofluoric aqueous solution is a 49% by weight hydrofluoric aqueous solution and wherein the water-based peroxide is a 30% by weight water-based peroxide.

5. A method of etching type II InAs/GaInSb superlattice epitaxial materials comprising:
   forming an etchant comprising a (2.5:4.5:16.5:280) solution by volume of HF:$H_2O_2$:$H_2SO_4$:$H_2O$;
   applying the etchant to a type II InAs/GaInSb superlattice epitaxial material;
   conducting the step of applying the etchant to a type II InAs/GaInSb superlattice epitaxial material at a temperature of about 20 degrees C.; and
   controlling the etching time by diluting with water.

6. The method of etching type II InAs/GaInSb superlattice epitaxial materials of claim 5 wherein the etching is conducted for about 60 to about 90 seconds and results in etch pits of about 4 to about 20 μm in diameter.

7. The method of etching type II InAs/GaInSb superlattice epitaxial materials of claim 6 wherein the etching does not involve stirring.

8. The method of etching type II InAs/GaInSb superlattice epitaxial materials of claim 7 wherein there is no surface treatment before etching.

9. The method of etching type II InAs/GaInSb superlattice epitaxial materials of claim 6 further including
   rinsing in deionized water; and
   drying using nitrogen gas.

10. The method of etching type II InAs/GaInSb superlattice epitaxial materials of claim 6 further including forming rectangular etch pits with crystallographic facets in locations containing dislocations in the crystal structure.

11. The method of etching type II InAs/GaInSb superlattice epitaxial materials of claim 10 wherein the resulting etch pits are oriented with the longest axis aligned along the [0$\bar{1}\bar{1}$] crystallographic direction.

12. The method of etching type II InAs/GaInSb superlattice epitaxial materials of claim 6 further including forming increasing the HF or $H_2O_2$ and producing an isotropic etch with rounded etch pits with crystallographic facets in locations containing dislocations in the crystal structure.

13. The method of etching type II InAs/GaInSb superlattice epitaxial materials of claim 6 further including
    forming etch pits with crystallographic facets in locations containing dislocations in the crystal structure; and
    correlating the shape of the etch pit to the type of dislocation or impurity.

14. The method of etching type II InAs/GaInSb superlattice epitaxial materials of claim 13 wherein a rectangular pit having bottom point symmetries reflecting dislocation direction correlates to threading dislocations and wherein twin rectangular etch pits are correlated to misfit dislocations with half loop termination points.

\* \* \* \* \*